United States Patent [19]

Davis

[11] Patent Number: 5,780,448
[45] Date of Patent: Jul. 14, 1998

[54] DNA-BASED VACCINATION OF FISH

[75] Inventor: Heather L. Davis, Ottawa, Canada

[73] Assignee: Ottawa Civic Hospital Loeb Research, Ottawa, Canada

[21] Appl. No.: 740,805

[22] Filed: Nov. 4, 1996

Related U.S. Application Data

[60] Provisional application No. 60/006,290 Nov. 7, 1995.

[51] Int. Cl.$^6$ .......................... C12N 15/00; A61K 39/12; A61K 39/29; A01N 43/04
[52] U.S. Cl. .................... 514/44; 435/69.3; 435/69.4; 435/69.5; 435/240.2; 435/320.1; 424/817; 424/199.1; 424/204.1; 424/201.1; 424/202.1; 424/227.1; 424/93.1; 536/23.1; 536/23.4; 536/23.72; 800/2
[58] Field of Search ........................... 424/93.1, 204.1, 424/199.1, 201.1, 202.1, 227.1, 817; 435/320.1, 69.3, 69.4, 69.5, 240.2; 536/23.1, 23.4, 23.72; 514/44; 800/2

[56] References Cited

U.S. PATENT DOCUMENTS

| | | |
|---|---|---|
| 4,009,259 | 2/1977 | Ament et al. . |
| 4,795,635 | 1/1989 | Peleg et al. . |
| 5,165,925 | 11/1992 | Leong . |
| 5,354,555 | 10/1994 | Leong . |

FOREIGN PATENT DOCUMENTS

| | | | |
|---|---|---|---|
| WO 91/13987 | 11/1991 | WIPO | C12N 15/47 |
| WO 94/27435 | 12/1994 | WIPO | A01N 25/26 |

OTHER PUBLICATIONS

Davis et al., 1994, Vaccine, vol. 12, pp. 1503–1509.
Hansen et al, 1991, FEBS, vol. 290, pp. 73–76.
Fynan et al, 1993, PNAS, vol. 90, pp. 11478–11482.
Lin et al, 1990, Circulation, vol. 82, No. 6, pp. 2217–2221.
Robinson et al, 1993, Vaccine, vol. 11, pp. 957–960.
Tang et al, 1992, Nature, vol. 356, pp. 152–154.
Cheng, L., et al., "In Vivo Promoter Activity And Transgene Expression In Mammalian Somatic Tissues Evaluated By Using Particle Bombardment," PNAS 90:4455–4459 (1993).

Davis, H., et al., "Direct Gene Transfer Into Skeletal Muscle In Vivo: Factors Affecting Efficiency of Transfer and Stability of Expression," Human Gene Therapy 4:151–159 (1993).
Davis, H., et al., "Plasmid DNA Is Superior To Viral Vectors For Direct Gene Transfer Into Adult Mouse Skeletal Muscle," Human Gene Therapy 4:733–740 (1993).
Felgner, P.L. et al. "Improved Cationic Lipid Formulations For In Vivo Gene Therapy," Annal New York Academy of Sciences pp. 126–139 (1995).
Leong, J.C. and J.L. Fryer., "Viral Vaccines For Aquaculture," Annual Rev. of Fish Diseases 3:225–240 (1993).
Munn, C.B., "The Use of Recombinant DNA Technology In The Development of Fish Vaccines," Fish and Shellfish Immunology 4:459–473 (1994).
Newman, S.G., "Bacterial Vaccines For Fish," Annual Rev. of Fish Diseases, pp. 145–185 (1993).
Sato, Y. et al., "Immunostimulatory DNA Sequences Necessary For Effective Intrademal Gene Immunization," Science 273:352–354.
Wolff, J.A., et al., "Direct Gene Transfer into Mouse Muscle in Vivo," Science 247:1465–68 (1990).
Wolff, J.A., et al., "Conditions Affecting Direct Gene Transfer Into Rodent Muscle In Vivo," Biotechniques 11(4):474–485 (1991).
Zhu, N., et al., "Systemic Gene Expression After Intravenous DNA Delivery Into Adult Mice," Science 261:209–211 (1993).

Primary Examiner—Mary E. Mosher
Assistant Examiner—Ali R. Salimi
Attorney, Agent, or Firm—Fish & Richardson, P.C.

[57] ABSTRACT

The present invention relates to methods of immunization of aquaculture species by introducing DNA expression systems into the aquaculture species. Such DNA expression systems preferably include DNA sequences encoding polypeptides of pathogens of species of aquaculture. The present invention also relates to methods of administration of DNA expression systems into aquaculture. Such methods include injection, spray, and immersion techniques. The methods of this invention are useful for prophylactic vaccination or therapeutic immunization of fin-fish, shellfish, or other aquatic animals against infectious diseases.

83 Claims, No Drawings

DNA-BASED VACCINATION OF FISH

Benefit of the United States Provisional Application No. 60/006.290, filed Nov. 7, 1995 is claimed herefor.

BACKGROUND OF THE INVENTION

Viral and bacterial diseases in fin-fish, shellfish or other aquatic lifeforms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic lifeforms facility. Prevention of disease is a more desired remedy to these threats to fish than intervention once the disease is in progress. Vaccination of fish is the only preventative method which may offer long-term protection through immunity.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Additionally, the efficiency of the immune response of fish can be affected by outside stresses, as is true in mammals. However, fish, unlike mammals, display a temperature-dependent development of protective immunity in response to antigens.

Most vaccines for fish have been developed against bacteria while there have been very few fish vaccines made for combating viral or parasitic diseases. Fish have been immunized by antigen-based immunization methods using live attenuated pathogens, killed whole pathogens, or more recently, in laboratory settings, recombinant proteins. While live attenuated vaccines induce good humoral and cell-mediated immune responses and can be administered orally or by immersion or injection, there is the important risk of reversion to a virulent form. Whole live attenuated vaccines are not preferred in industrial farming due to the risk of contaminating other fish—a live attenuated vaccine which may be generally safe for the target species of fish may be virulent in other species of fish.

Fish vaccines using whole killed bacteria (i.e. bacterins) or recombinant proteins from pathogens expressed in cell lines (subunit vaccines) have the disadvantage of inducing short-lived immune responses. Injected antigen, including recombinant protein, is processed solely in an exogenous form usually causing induction of a humoral response (i.e., production of antibodies) but often a failure to induce cell-mediated immunity (i.e., cytotoxic T-cells).

Another disadvantage of whole killed and subunit vaccines is that they almost always must be injected and they require an adjuvant to induce an effective immune response. Intramuscular injections of these adjuvants can cause granuloma formation which scars the flesh and lowers the market value of the fish. Intraperitoneal injection of adjuvants may cause adhesions between the viscera which can affect the health of the fish and retard fish growth.

Recombinant protein vaccines are difficult and expensive to make especially if the protein must be purified. For example, bacterially-expressed recombinant proteins may form inclusion bodies from which recovery of protein in correct configuration may be low or nonexistent. Induction of an immune response may require that the antigenic protein be correctly glycosylated and folded, which may not be accomplished in a cell other than an animal cell.

Some of the current methodologies for administering vaccines are not technically or economically practical. For example, direct injection of recombinant and whole killed pathogen vaccines into the fish is labor intensive and expensive relative to the future market value of the fish. Furthermore, injection needles can cross-infect fish with contaminating pathogenic organisms, and accidental injection of humans can cause severe or fatal infections and anaphylactic reactions. Moreover, noninjurious injection of small fish is very difficult, especially in young fry, which are particularly susceptible to disease.

A less expensive and easier method which has been used to administer killed viral or bacterial vaccines is an oral method wherein the vaccine is added directly to the water or incorporated into fish food. Oral vaccines have historically shown inconsistent and relatively low levels of protection suggesting that they may be best used as a method of revaccination.

Genes have been introduced directly into animals by using live viral vectors containing particular sequences from an adenovirus, an adeno-associated virus, or a retrovirus genome. The viral sequences allow the appropriate processing and packaging of a gene into a virion, which can be introduced to animals through invasive or non-invasive infection. Viral vectors have several disadvantages. Viral vectors being live pathogens, still carry the risk of inadvertent infection. Furthermore, proteins from viral vector sequences induce undesirable inflammatory or other immune responses which may prevent the possibility of using the same vector for a subsequent vaccine or boost. Viral vectors also limit the size of the target gene that can be expressed due to viral packaging constraints.

Naked DNA transfects relatively efficiently if injected into skeletal muscle but poorly or not at all if injected into other tissues (Wolff et al., *Science* 247:1465–1468 (1990), incorporated herein by reference). Plasmid DNA coated onto the surface of small gold particles and introduced into the skin by a helium-driven particle accelerator or "gene-gun" can directly transfect cells of the epidermis and dermis (Pecorino and Lo, *Current Biol.*, 2:30–32 (1992), which is incorporated herein by reference).

DNA has also been introduced into animal cells by liposome-mediated gene transfer. DNA-liposome complexes, usually containing a mixture of cationic and neutral lipids, are injected into various tissues or instilled into the respiratory passages. Nabel et al., *Hum. Gene Ther.*, 3:649–656 (1992), which is incorporated herein by reference, have shown that liposomes may be used to transfect a wide variety of cell types by intravenous injection in mammals. In addition, liposome-mediated gene transfer has been used to transfer the cystic fibrosis transmembrane conductance gene into the nasal epithelium of mice and humans suffering from cystic fibrosis (Yoshimura et al., *Nucleic Acids Reg.*, 12:3233–3240 (1992) and Caplan et al., *Nature Med.*, 1:39–46 (1995), respectively, both of which are incorporated herein by reference.

Substances may also be administered using biodegradable microspheres composed of polymers such as polyester poly (lactide-co-glycolide) (Marx et al., *Science*, 260:1323–1328 (1993), incorporated herein by reference). It is notable that these particles can survive the upper digestive system and arrive intact in cells of gut-associated lymphoid tissue (Eldridge et al., *Adv. Exp. Med. Biol.*, 251:191–202 (1989), incorporated herein by reference). Biodegradable microspheres have been used to deliver recombinant antigens, toxoids or attenuated virus into mammals by systemic and oral routes (O'Hagan et al., *Immunology* 73:239–242 (1991); O'Hagen et al., *Vaccine* 11:149–154 (1993); Eldridge et al., *Mol. Immunol.* 228:287–293 (1991) incorporated herein by reference). They may also be useful to deliver recombinant plasmid DNA to gut-associated lymphoid tissue for the purpose of immunization.

While most work has been carried out on mammals, plasmid DNA encoding reporter genes have been successfully introduced into fish by intramuscular injection (Hansen et al., *FEBS Lett.* 290:73–76 (1991), incorporated herein by reference). Thus, cells in fish can express proteins from a foreign gene with the same types of vector constructs (i.e., backbones, promoter and enhancer elements) that are used in mammals.

The induction of an immune response to a protein expressed from an introduced gene was first suggested by Acsadi et al., *New Biologist* 3:71–81 (1991), which is incorporated herein by reference, who found that after plasmid DNA transfer into rat cardiac muscle, reporter gene expression was transient but could be prolonged by treatment with an immuno-suppressant. Subsequently, it was shown that antibodies were induced in rodents against human growth hormone (Tang et al., *Nature*, 356:152–154 (1992); Eisenbraun et al., *DNA Cell. Biol.*, 12:791–797 (1993), both of which are incorporated herein by reference) or human α-antitrypsin (Tang et al., *Nature*, 356:152–154 (1992), also incorporated herein by reference) when these proteins were expressed from DNA coated onto gold particles and introduced into cells of the skin by bombardment.

DNA-based immunization refers to the induction of an immune response to an antigen expressed in vivo from a gene introduced into the animal. This method offers two major advantages over classical vaccination in which some form of the antigen itself is administered. First, the synthesis of antigen in a self-cell mimics in certain respects an infection and thus induces a complete immune response but carries absolutely no risk of infection. Second, foreign gene expression may continue for a sufficient length of time to induce strong and sustained immune responses without boost.

Several mammalian animal models of DNA-based immunization against specific viral, bacterial or parasitic diseases have been reported. These include influenza [(Fynan et al., *Proc. Nat'l Acad. Sci. USA*, 90:11478–11482 (1993); Montgomery et al., *DNA Cell. Biol.*, 12:777–783 (1993); Robinson et al., *Vaccine*, 11:957–960(1993); Ulmer et al., *Science*, 259:1745–1749 (1993)], HIV [Wang et al. (1993)], hepatitis B [Davis et al., *Hum. Molec. Genet.*, 2:1847–1851 (1993)], malaria [Sedagah et al., *Proc. Nat'l Acad. Sci. USA*, 91:9866–9870 (1994)], bovine herpes [Cox et al., *J. Virol*, 67:5664–5667 (1993)], herpes simplex [Rousse et al., *J. Virol.*, 68:5685–5689 (1994); Manicken et al. *J. Immunol.*, 155:259–265 (1995)], rabies [Xiang et al., *Virology*, 199:132–140 (1994)]; lymphocytic choriomeningitis [Yokoyama et al., *J. Virol.*, 6964:2684–2688 (1995)] and tuberculosis [Lowrie et al., *Vaccine*, 12:1537–1540 (1994)], all of which are incorporated herein by reference. In most of these studies a full-range of immune responses including antibodies, cytotoxic T lymphocytes (CTL), T-cell help and (where evaluation was possible) protection against challenge was obtained. In these studies naked DNA was introduced by intramuscular or intradermal injection with a needle and syringe or by instillation in the nasal passages, or the naked DNA was coated onto gold particles which were introduced by a particle accelerator into the skin.

There is a need for novel systems to vaccinate fin-fish, shellfish, and other aquatic animals against diseases. These systems should be inexpensive to produce and administer, avoid the use of live, attenuated organisms, and induce strong and long-lasting immunity preferably without boost and with induction of both antibodies and cell-mediated immunity. More preferably, the system should be applicable to small fish, be less stressful to fish during administration, and have the capacity of simultaneously immunizing many animals for reduced labor-related costs.

SUMMARY OF THE INVENTION

The present invention relates to the immunization of cultured fin-fish, shellfish, or other aquatic animals ("aquaculture species") by DNA expression systems to overcome many disadvantages associated with antigen-based vaccines. The present invention relates to introduction of DNA plasmids (alone or in a formulation) containing sequences encoding antigenic components of viral, bacterial or parasitic diseases by transfection into aquaculture species. The methods and compositions of this invention are useful for immunization (i.e., for prophylactic vaccination or therapeutic immunization) of fin-fish, shellfish or other aquatic animals against infectious diseases. The DNA sequences according to this invention are preferably present in vectors capable of inducing protein expression of these sequences (i.e. expression vectors) and may be administered alone or in combination with other DNA sequences in the same or other expression vectors or as oligonucleotides. These additional DNA sequences may encode cytokines, costimulatory molecules, or may include immunostimulatory sequences (e.g., CpG motifs). The DNA sequences may also be given with other adjuvants, such as alum.

The present invention also relates to methods of administration of DNA expression vectors to aquaculture species, which may or may not encode polypeptides from pathogens. DNA vectors of this invention may be administered to aquaculture species by oral route, injection, spray, or immersion. In a preferred embodiment, the DNA expression vectors of this invention are administered by immersion techniques or automated injection devices.

DESCRIPTION OF THE INVENTION

The present invention provides for methods and compositions for immunizing cultured fin-fish, shellfish, and other aquatic animals against infection by viral, bacterial or parasitic pathogens. In basic outline, DNA encoding a polypeptide component of a pathogen is introduced into an animal, and the polypeptide is expressed in cells of the animal, thus inducing an immune response that confers protection against natural infection by the pathogen or helps overcome an ongoing and possibly chronic infection.

In a preferred embodiment, the present invention provides a method for immunizing cultured fin-fish, shellfish, or other aquatic animals against disease, comprising immersion of the animals in an aqueous solution containing formulated plasmid DNA encoding one or more antigenic determinants of an infectious agent (regardless of codon usage), whereby the DNA enters cells of the animal where it is expressed leading to induction of immune responses. The immunization procedure may be prophylactic to prevent infection from occurring or may be therapeutic to treat pre-existing infections.

Few anti-viral vaccines have been marketed for fish. This is largely due to the difficulty of growing virus in culture for the production of whole killed viral vaccines or safe attenuated strains of virus. Antigen-based vaccines using purified recombinant proteins are difficult and expensive to produce in large scale and may have poor immunogenicity in fish.

DNA-based immunization has several advantages. The antigenic protein is synthesized in vivo giving rise to both humoral and cell-mediated (cytotoxic T lymphocytes) immune responses. However, unlike live attenuated pathogens, which also synthesize protein in vivo. DNA vaccines carry no risk of inadvertent infection. Unlike antigen-based immunization. DNA-based vaccination does not require the use of traditional adjuvants to generate an effective immune response. Furthermore, DNA used in the methods of this invention is inexpensive and easy to manufacture and purify.

DNA-based immunization also allows the host animal to produce foreign antigens within its own tissue thereby resulting in several advantages. One advantage is the efficient presentation of the foreign antigen to the immune system due to the expression of a protein within a self-cell, which could be an antigen-presenting cell. Another advantage is the correct folding, protein modification, and disulfide bonding of a protein expressed in a host cell, especially for viral proteins, which are normally produced in cells of hosts. Recombinant viral proteins synthesized in bacterial or yeast cells may be incorrectly post-translationally modified and are often massed in inclusion bodies, which make the proteins difficult to purify or ineffective if administered in unpurified form.

Immune responses in fish are temperature dependent. Antigen-based vaccines may give rise to sub-optimal immune responses if such vaccines are given at the wrong temperature. DNA-based immunization is advantageous because expression of the antigenic protein could continue over a long period until such time as to stimulate an immune response when the temperature is optimal.

Another advantage of prolonged synthesis of antigen is the induction of immune responses as soon as the immune system is mature. Fish may be unable to induce sufficient immune responses at a young age. For example, trout and halibut may not produce lymphoid cells until as late as ten and thirty days after hatching, respectively, and T-dependent immune responses do not appear until months after hatching. Using the methods of this invention, expression of foreign protein in fish can continue at least four months after transfection indicating that DNA-based immunization may be preferred for vaccination of young fish.

The term "vaccine" herein refers to a material capable of producing an immune response. A vaccine according to this invention would produce immunity against disease in cultured fin-fish, shellfish and other aquatic species. One of skill in the art would readily appreciate that activation of CTL activity resulting from in vivo synthesis of antigen would produce immunity against disease not only prophylactically but also therapeutically (after development of disease in culture).

Aquaculture species treated by methods of this invention will include a diversity of species of cultured fin-fish, shellfish, and other aquatic animals. Fin-fish include all vertebrate fish, which may be bony or cartilaginous fish. A preferred embodiment of this invention is the immunization of fin-fish. These fin-fish include but are not limited to salmonids, carp, catfish, yellowtail, seabream, and seabass. Salmonids are a family of fin-fish which include trout (including rainbow trout), salmon, and Arctic char. Examples of shellfish include, but are not limited to, clams, lobster, shrimp, crab, and oysters. Other cultured aquatic animals include, but are not limited to eels, squid, and octopi.

Purification of DNA on a large scale may be accomplished by anion exchange chromatography (for example, resins manufactured by Qiagen. U.S. FDA Drug Master File (DMF-6224)).

DNA which is introduced to aquaculture species will encode foreign polypeptides (e.g., those derived from viral, bacterial or parasitic pathogens). Polypeptides of this invention refer to complete proteins or fragments thereof, including peptides which are epitopes (e.g., a CTL epitope) associated with an infectious virus, bacterium or parasite.

DNA sequences encoding a complete or large parts of an antigenic protein are preferred where humoral immunity is desired rather than DNA sequences encoding smaller parts, such as only CTL epitopes, as are preferred where cell-mediated immunity is desired and humoral immunity may be deleterious. In preferred embodiments, the DNA sequences encoding polypeptides of viral pathogens may be selected from the group consisting of glycoprotein (G) or nucleoprotein (N) of viral hemorrhagic septicemia virus (VHSV); G or N proteins of infectious hematopoietic necrosis virus (IHNV); VP1, VP2, VP3 or N structural proteins of infectious pancreatic necrosis virus (IPNV); G protein of spring viremia of carp (SVC); and a membrane-associated protein, tegumin or capsid protein or glycoprotein of channel catfish virus (CCV).

In other preferred embodiments, the DNA sequences encoding polypeptides of bacterial pathogens may be selected from the group consisting of an iron-regulated outer membrane protein, (IROMP), an outer membrane protein (OMP), and an A-protein of *Aeromonis salmonicida* which causes furunculosis, p57 protein of *Renibacterium salmoninarum* which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an iron-regulated outer membrane protein (IROMP), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of Ichthyophthirius; and a structural and regulatory protein of *Cytophaga columnari*; and a structural and regulatory protein of Rickettsia.

In yet another preferred embodiment, the DNA sequences encoding polypeptides of a parasitic pathogen may be selected from one of the surface antigens of Ichthyophthirius.

The methods of this invention could also be used to introduce plasmid vectors encoding polypeptides endogenous to the animal, but which might be normally present in low concentrations (e.g., growth hormones). In this case the expression proteins would serve a physiological role (i.e. enhanced growth) rather than induce an immune response.

Vectors useful in the making of expression plasmids include, but are not limited to, vectors containing constitutive promoters, inducible promoters, tissue-specific promoters, or promoters from the gene of the antigen being expressed. Constitutive promoters may include strong viral promoters, for example, promoter sequences from cytomegalovirus (CMV), Rous sarcoma virus (RSV), simian virus-40 (SV40), or herpes simplex virus (HSV). Tissue-specific promoters may include the muscle beta-actin promoter or the thymidine kinase promoter. An inducible or regulatable promoter, for example, may include a growth hormone regulatable promoter, a promoter under the control of lac operon sequences or an antibiotic inducible promoter or a Zinc-inducible metallothionein promoter.

The vector should include an expression control sequence comprising a promoter (e.g., inducible or constitutive promoters described above) DNA sequence, and may include, but is not limited to, an enhancer element, an RNA processing sequence such as an intronic sequence for splicing of a transcript or a polyadenylation signal (e.g., from simian virus-40 (SV40) or bovine growth hormone (BGH)), a signal sequence for secretion of the expressed protein, or one or more copies of immunostimulatory DNA sequences known as CpG motifs. The vector should also include one or more of the following DNA sequences: bacterial origin of replication sequences, a selectable marker, which may be for antibiotic resistance (e.g., kanamycin) or for non-antibiotic resistance (e.g., β-galactosidase gene).

Oligonucleotides having unmethylated CpG dinucleotides have been shown to activate the immune system (A. Krieg, et al., "CpG motifs in Bacterial DNA Trigger Directed B Cell Activation" Nature 374:546–549 (1995)). Depending on the flanking sequences, certain CpG motifs may be more immunostimulatory for B cell or T cell responses, and preferentially stimulate certain species. Copies of CpG motifs in DNA expression vectors act as adjuvants facilitating the induction of an immune response against an expressed protein. A CpG motif, a stretch of DNA containing CpG dinucleotides within a specified sequence, may be as short as 5–40 base pairs in length. Multiple CpG motifs may be inserted into the non-coding region of the expression vector. When a humoral response is desired, preferred CpG motifs will be those that preferentially stimulate a B cell response. When cell-mediated immunity is desired, preferred CpG motifs will be those that stimulate secretion of cytokines known to facilitate a CD8+ T cell response.

Other CpG motifs have be found to inhibit immune responses. In a preferred embodiment of the application, these immunoinhibitory CpG motifs would be removed or mutated in a DNA expression vector used by the methods of this invention, without disrupting the expression of polypeptides therefrom.

An additional preferred embodiment of this invention relates to the administration of a vector containing one or more different DNA sequences, one sequence encoding an antigen and the others encoding polypeptides which may or may not be antigenic. For example, the vector may encode two antigens from the same pathogen. Alternatively, the different antigen(s) may induce an immune response against a different pathogen and thus serve as a multivalent vaccine. Alternatively, the other polypeptides may serve to enhance an immune response against a targeted pathogen (e.g., helper epitopes, cytokines, carrier polypeptides, cholera toxin subunits, or other immunostimulants).

When two or more polypeptide-encoding DNA sequences are present in one vector, the transcription of each antigen-encoding DNA sequence may be directed from its own promoter. Alternatively, one promoter may drive the expression of two or more antigen-encoding DNA sequences joined in frame to each other to express a fusion protein. For example, VP2 and VP3 proteins of infectious pancreatic necrosis virus (IPNV) may be fused. In another embodiment, DNA sequences encoding two or more antigens from different diseases may be joined to form a multivalent vaccine when expressed.

Alternatively, a DNA sequence encoding an antigenic polypeptide may be fused to a DNA sequence encoding a carrier polypeptide. In a preferred embodiment, the carrier polypeptide may contain one or more envelope proteins of the hepatitis B virus, preferably from the human hepatitis B virus. In a more preferred embodiment, the envelope proteins of hepatitis B virus will be the small and major protein (also referred to as surface antigen).

In another embodiment, each polypeptide-encoding DNA sequence in the vector may be under the control of its own promoter for expression of two or more non-fused polypeptides.

Alternatively, the DNA sequences encoding additional antigens may be administered by using a second vector containing such sequences. Such sequences may encode antigens from the same pathogen or different pathogens, or cytokines, cholera toxin subunits, or other immunostimulants. Such a vector may be administered concurrently or sequentially with the first expression vector. A preferred embodiment of this invention is the concurrent administration of expression vectors. One vector may be induced to express protein simultaneously with or after expression of protein from the other vector.

In yet another embodiment of this invention, antigen-expressing vectors may be administered concurrently with an antigen-based vaccine such as a recombinant protein or whole-killed vaccine. In a preferred embodiment, the antigen-expressing vector is administered simultaneously with a protein antigen (i.e. recombinant protein or whole killed pathogen). Another preferred embodiment would be to first administer a DNA vaccine to prime the immune response followed by administration of the protein antigen two to eight weeks later, preferably orally or by immersion, to boost the immune response.

The DNA used in the method of this invention is preferably purified plasmid DNA(s) simply dissolved in an aqueous solution or in a formulation. One of skill in the art would readily appreciate how to formulate DNA used in the methods of this invention with known transfection reagents such as cationic liposomes, fluorocarbon emulsions, cochleates, tubules, gold particles, biodegradable microspheres, or cationic polymers.

Liposomes useful for transfection of DNA of this invention include commercially available liposomes and liposomes containing either cationic lipids or cationic polymers. In a preferred embodiment of this invention, liposomes would include a mixture of a neutral lipid such as dioleoylphosphatidylethanolamine (DOPE) or cholesterol and a cationic lipid.

In a more preferred aspect of the invention, liposomes would include a mixture of cationic polymers and neutral lipids such as DOPE or cholesterol. Such liposomes may be prepared as described herein and in United States Provisional Patent Application entitled, "A Novel Class of Cationic Reagents for High Efficient and Cell-Type-Specific Introduction of Nucleic Acids into Eukaryotic Cells", incorporated by reference herein. Unlike cationic lipids, cationic polymers do not have ester-linkages and have greater stability in vivo as a result. Cationic polymers (also referred to as dendrimers) may be dimeric, cyclic, oligomeric, or polymeric in structure.

Cationic polymers in an aqueous solution without neutral lipids are also preferred transfection reagents according to the preferred embodiments of this invention. Cationic polymers have been shown to work well for transfecting fish cells in vitro with plasmids expressing fish pathogen antigens (see Table 1, Example 1).

Cochleates, which are stable phospholipid-calcium precipitates composed of phosphatidylserine, cholesterol and calcium are desirable non-toxic and non-inflammatory transfection reagents that can survive the digestive system. Biodegradable microspheres composed of polymers such as polyester poly(lactide-co-glycolide) have been used to microencapsulate DNA for transfection.

Tubules have been previously described in the literature as lipid-based microcylinders consisting of helically wrapped bilayers of lipid, the edges of which are packed together. DNA may be placed in the hollow center for delivery and controlled release in animals.

With immersion, DNA may enter cells of the epithelium of the skin, the gills or the gut wall. With injection, DNA may enter muscle cells or other cells in muscle tissue (e.g. fibroblasts, immune cells) or cells of viscera within the intraperitoneal cavity. DNA may then be expressed in these transfected cells leading to induction of appropriate immune responses in regional or systemic lymphoid tissue.

The invention provides for pharmaceutical compositions comprising DNA vaccines in an amount effective for the treatment and prevention of diseases caused by pathogens of aquaculture species. According to another embodiment, the pharmaceutical compositions of this invention further comprise a second DNA vaccine, an adjuvant, a recombinant protein, a transfection reagent, or some combination thereof.

Methods of this invention may be useful in the immunization of aquaculture species against many pathogens. Such pathogens include but are not limited to hemmorrhagic septicemia virus, infectious hematopoietic necrosis virus, infectious pancreatic necrosis virus, virus causing spring viremia of carp, channel catfish virus (*Herpesvirus ictaluri*), grass carp hemorrhagic virus, nodaviridae such as nervous necrosis virus or striped jack nervous necrosis virus, infectious salmon anaemia virus, *Aeromonis salmonicida, Renibacterium salmoninarum,* Yersinia, Pasteurella (including *piscicida*), Vibrosis (including *anguillarum* and *ordalii*), Edwardsiella (including *ictaluri* and *tarda*), Streptococci, and Ichthyophthirius.

In one embodiment of this invention, recombinant plasmid DNA is introduced into animals orally. DNA for oral use may be formulated with biodegradable microspheres, fluorocarbon emulsions, cochleates, or tubules. This is a non-stressful method of immunizing aquaculture species by which DNA may be coated onto or milled into feed in the form of a paste or liquid suspension or incorporated into gelatin capsules and introduced into the environment of the aquaculture species. Preparations of DNA for oral use may include lactose and corn starch. The DNA can be used with or without products to enhance entry into cells of the gut epithelium or more deeply situated cells.

In another embodiment, pure recombinant plasmid DNA is introduced into animals by injection with a needle or a jet-injection system, which does not have a needle. Injection areas of the fin-fish include but are not limited to intraperitoneal, intramuscular, and subcutaneous areas of the fish. In a preferred embodiment, large fin-fish are immunized by injection methods of this invention. Typically, fish are injected with 0.1–0.5 ml of a solution containing DNA. DNA may be injected in a pure form or may be formulated with liposomes, cationic polymers, fluorocarbon emulsions, cochleates, or tubules.

In yet another embodiment of this invention, pure DNA is introduced into a fin-fish by particle bombardment. This method introduces DNA-coated gold particles into the epidermis of a fin-fish using a "gene-gun", which uses compressed helium to shoot the gold particles at high speed into the skin. This method has been shown to be particularly efficient for induction of cell-mediated immune responses with small quantities of DNA in mice.

In another embodiment of this invention, plasmid DNA is introduced to fish by spray. Typically, fish are exposed to spray for at least 2 seconds. Fish may pass through a mist of DNA solution by forcing the vaccine through high-pressure paint-sprayer-type nozzles. Typically, any pressure up to 90 psi is satisfactory. Due to the number of pounds of fish per unit volume that can be vaccinated by spray, it may be more economical to immunize larger fish by this method than by immersion. The DNA can be used with or without products to enhance entry into cells of the skin. For example, the DNA may be associated with liposomes or cationic polymers.

In a more preferred embodiment of this invention, a large number of animals can be immunized simultaneously by immersion in a solution containing DNA. In one embodiment, fish are dip-netted into suspensions containing DNA formulations (e.g., DNA formulated with cationic polymers or liposomes) for at least several seconds. The fish are then returned to the holding tanks in which they develop immunity. In another embodiment, fin-fish, shellfish, or other aquatic animals are placed into tanks containing a relatively small volume of water. Concentrated DNA formulations (e.g., DNA formulated with cationic polymers or liposomes) is added to the tank, and animals are left for a period of time up to several hours before the tank is refilled with water to restore the normal aquatic environment. This method of immersion is preferred for the immunization of small fry, which cannot be immunized by direct injection.

The amount of the expression plasmid DNA that may be combined with a carrier material to produce a single dosage form will vary depending upon the host treated, and the particular mode of administration. It should be understood, however, that a specific dosage and treatment regimen for any particular fish will depend upon a variety of factors, including the expression of the particular plasmid DNA employed, the stability and activity of the particular protein or peptide expressed, age, body weight, general health, species of fish, the progress of the disease being treated, and nature of the disease being immunized against or dreaded. The amount of expression plasmid DNA may also depend upon whether other therapeutic or prophylactic agents including additional expression plasmid DNAs and adjuvants, if any, are co-administered with the expression plasmid.

Without being bound by the values listed below, dose ranges for the administration of DNA used in the methods of this invention may be generalized as follows. For immunization of fish via oral routes, 0.1 to 50 µg DNA per fish administered over several consecutive days may be used. For DNA-based immunization by intramuscular or intraperitoneal injection, 0.1 to 10 µg of DNA may be used. For spray immunization, a volume of 1 ml per fish of 0.1 to 10 mg/ml DNA solution may be useful. Fish immunized by immersion methods of this invention may be incubated in a 1 to 100 µg/ml DNA solution at a volume sufficient for fish to survive for a time period necessary for uptake of DNA to produce an immune response by the fish. An effective dosage range for immunization of fish via gene-gun route may be 10 ng to 1 µg.

Adjuvants for immunization are well known in the art and suitable adjuvants can be combined with the DNA sequences described herein by a person skilled in the art to form a pharmaceutical composition. Oil adjuvants are least desirable for the methods of this invention because they create undesirable side-effects such as visceral adhesions (which can restrict growth) and melanized granuloma formations (which can lower the grade of the fish at market) and because they cannot form a homogeneous mixture with DNA preparations. DNA-based immunization does not require oil adjuvants and thus avoids these undesirable effects.

Adjuvants used in immunization with DNA expression plasmids of this invention may include alum or a DNA molecule having unmethylated CpG dinucleotides therein (also referred to as CpG adjuvant). Oligonucleotides having unmethylated CpG dinucleotides have been shown to activate the immune system (A. Krieg, et al., "CpG motifs in Bacterial DNA Trigger Directed B Cell Activation" Nature 374:546–549 (1995)). CpG motifs may be inserted into a plasmid DNA vaccine vector, and replicated in bacteria thereby allowing the CpG motifs to retain their unmethylated form. As such, administration of a CpG adjuvant cloned into plasmid vectors would be simultaneous with the administration of a plasmid DNA vaccine. Alternatively, a CpG adjuvant in the form of free oligonucleotides may be administered before, during or after the administration of a plasmid DNA vaccine.

Oligonucleotides having CpG motifs may be optionally modified at their phosphodiester linkages for stability purposes. Such modifications are well known by those of skill in the art. For example, phosphodiester bonds in an oligonucleotide may be replaced by phosphorothioate linkages.

The present invention also includes pharmaceutical products for all of the uses contemplated in the methods described herein. For example, a pharmaceutical product comprising pure plasmid DNA vector or formulations thereof, operatively coding for an immunogenic polypeptide or peptide, may be prepared in physiologically acceptable administrable form (e.g., saline). The pharmaceutical product may be placed in a container, with a notice associated with the container in the form prescribed by a governmental agency regulating the manufacture, use or sale of pharmaceuticals, which notice is reflective of approval by the agency of the form of the DNA for veterinary administration. Such notice, for example, may be labeling approved by the Biologics Division of Agriculture and Agri-Food Canada or the United States Department of Agriculture (USDA) or the approved product insert.

In order that this invention may be more fully understood, the following examples are set forth. These examples are for the purpose of illustration only and are not to be construed as limiting the scope of the invention in anyway.

EXAMPLES

Example 1

Cloning of DNA encoding Antigenic Proteins Into Plasmid DNA Vectors

DNA encoding proteins of fish pathogens is useful in developing DNA fish vaccines. Table 1 below recites fish pathogen protein expression plasmids. Table 1 describes nucleotide sequences encoding proteins from pathogens cloned into vectors having the cytomegalovirus promoter (CMV), i.e., pcDNA3 (from Invitrogen) or a vector containing the CMV promoter and intron A of CMV to promote better expression of protein (pCMV$_A$ vector). For example, genetic sequences coding for the major glycoprotein (G) or nucleoprotein (N) of the viral hemorrhagic septicemia virus (VHSV) were cloned into the EcoRI site of either the pcDNA3 or pCMV$_A$ vector. Nucleotide sequences encoding the VP2 and VP3 structural proteins of the infectious pancreatic necrosis virus (IPNV) were cloned into same vectors. The gene encoding the ferric siderophore receptor (fstA) of *Aeromonas salmonicida* has also been cloned into exp ression vectors. The fstA protein is one of several possible iron-regulated outer membrane proteins that could be expressed as an antigen from a DNA vaccine.

TABLE 1

| Plasmid | Vector | Antigen | Pathogen |
|---|---|---|---|
| pCMV-G | pcDNA3 (EcoRI site) | G glycoprotein (#1-1565)* | viral hemorrhagic septicemia virus |
| $pCMV_A$-G | $pCMV_A$ vector (EcoRI site) | G glycoprotein (#1-1565)* | viral hemorrhagic septicemia virus |
| pCMV-N | pcDNA3 (EcoRI site) | N nucleoprotein (#92-1306)* | viral hemorrhagic septicemia virus |
| $pCMV_A$-N | $pCMV_A$ vector (EcoRI site) | N nucleoprotein (#92-1306)* | viral hemorrhagic septicemia virus |
| pCMV-VP2 | pcDNA3 (HindIII/XbaI site) | VP2 (#117-1760)* | infectious pancreatic necrosis virus |
| $pCMV_A$-VP2 | $pCMV_A$ vector (SalI/XbaI) | VP2 creatic (#117-1760)* | infectious pan- necrosis virus |
| pCMV-VP3 | pcDNA3 (EcoRI/XbaI site) | VP3 (#2325-3011)* | infectious pancreatic necrosis virus |
| $pCMV_A$-VP3 | $pCMV_A$ vector (EcoRI/XbaI site) | VP3 (#2325-3011)* | infectious pancreatic necrosis virus |
| pCMV-fstA | pcDNA3 (EcoRI/XbaI site) | IROMP fstA (#76-2630)* | *Aeromonis salmonicida* |
| $pCMV_A$-fstA | $pCMV_A$ vector (EcoRI/XbaI slte) | IROMP fstA (#76-2630)* | *Aeromonis salmonicida* |

*# indicates the nucleotide sequences within the genome of the pathogen which have been cloned to code for the antigen

Example 2

Expression of Foreian Protein In Fish Injected with Pure Plasmid DNA Vector The pCMV-luc plasmid used in the following experiments contains the luciferase reporter gene (luc) under the control of the cytomegalovirus promoter. Purified plasmid DNA was prepared by using commercially available Qiagen DNA purification columns. The purified plasmid DNA was then dissolved in endotoxin-free Dulbecco's phosphate buffered saline (DPBS) without calcium chloride or magnesium chloride, or in 0.15M NaCl dissolved in deionized distilled water for a final concentration of 0.001 mg/ml to 5 mg/ml DNA. Fish were anaesthetized with 0.168 mg/ml tricaine (3-amino benzoic acid ethylester) in water or by placing the fish on ice for 30–60 seconds before injection. Trout and zebra fish were injected intramuscularly between the dorsal fin and the lateral line with 10 μl of the DNA solution.

Luciferase activity was measured in the muscle and gills 2.5 days after injection. Rainbow trout were euthanized by an overdose of tricaine (0.1% w/v). Zebra fish were killed by immersion in ice. The muscle or gills of the fish were removed on ice, homogenized, centrifuged to pellet cellular debris, and the supernatants containing soluble proteins were assayed for luciferase activity. Luciferase assays were carried out using a kit commercially available from Promega Corporation. Light emission in relative light units (RLU) was quantitated by a luminometer (Analytical Luminescence Laboratory) over a ten second interval and background values from control samples were subtracted. The concentration of protein in the supernatants was determined and luciferase activity was expressed as RLU/sec/mg protein.

The results summarized in Table 2 (below) indicate that purified plasmid DNA can efficiently transfect fish cells after intramuscular injection. Nanogram amounts of plasmid DNA were able to induce detectable protein expression in both the injected muscle as well as more distant cells (e.g., in gills), showing that different types of cells, possibly including antigen presenting cells (APC), are transfectable by plasmid DNA and are capable of synthesis of foreign protein. Cells distant to the site of injection (i.e. gills) expressed lower amounts of protein than the injected muscle cells. Zebra fish and trout are not closely related species of fish. Therefore, the results in Table 2 indicate that most species of fish could take up and express foreign proteins from injected plasmids.

TABLE 2

| Dose of DNA | Luciferase Activity (RLU/sec/mg of protein)* | | | |
|---|---|---|---|---|
| | Trout | | Zebra Fish | |
| (μg) | Muscle | Gills | Muscle | Gills |
| 0.01 | 3,449 (±1548) | 4 (±3) | 502 (±307) | 18 (±8) |
| 0.1 | 22,768 (±12,708) | 36 (±14) | 11,665 (±2,989) | 94 (±66) |
| 1 | 78,408 (±51,523) | 618 (±567) | 826,486 (±368,790) | 228 (±115) |
| 10 | 280,051 (±172,749) | 982 (±743) | 199,285 (±97,134) | 833 (±621) |
| 50 | 417,226 (±165,164) | 980 (±393) | 145,891 (±85,645) | 5,519 (±4791) |

*mean ± standard error of mean (n = 10 fish per group)

Example 3

Kinetics And Longevity of Foreign Gene Expression in Fish

One microgram of pCMV-luc plasmid in 10 μl of saline was injected intramuscularly into adult zebra fish and 3–4 month old rainbow trout as previously described in Example 2. Luciferase activity in the muscle and gills of the injected fish was determined at various times between 2.5 days and 8 weeks using the methods described in Example 2. In Table 3 (below), the plasmid DNA directs protein expression within days of injection and protein expression in post-mitotic muscle remains stable for at least eight weeks. Luciferase expression in the gills falls off over time, possibly due to cell turnover.

TABLE 3

| Time | Luciferase Activity (RLU/sec/mg of Protein)* | | | |
|---|---|---|---|---|
| | Trout | | Zebra Fish | |
| (days) | Muscle | Gills | Muscle | Gills |
| 0 | 0 | 0 | 0 | 0 |
| 2.5 | 78,408 (±51,523) | 618 (±567) | 2,107,048 (±1,281,284) | 8,705 (±6853) |
| 14 | 54,004 (±19,411) | 211 (±133) | 4,160,080 (±2,553,955) | 6,965 (±3,672) |
| 28 | 90,686 (±46,044) | 39 (±20) | 5,236,613 (±4,536,744) | 6,056 (±4048) |
| 56 | 18,219 (±11,785) | 30 (±23) | 6,395,781 (±1,764,195) | 3,246 (±1,040) |

*mean ± standard error of mean (n = 10 fish per group)

Example 4

Kinetics and Longevity of Foreign Gene Expression in Zebra Fish

Zebra fish were injected intramuscularly with 0.1 μg of purified plasmid pCMV-luc DNA in 10 μl of saline as previously described in Example 2. The results from Table 4 (below) indicate that even ten-fold less DNA than used in Example 3 is capable of producing detectable levels of protein for at least sixteen weeks. The results also indicate that protein expression begins within hours after injection.

TABLE 4

| Time | Luciferase Activity (RLU/sec/mg of Protein)* | |
|---|---|---|
| (days) | Muscle | Gills |
| 0.16 | 64 (±35) | 1 (±1) |
| 0.33 | 1,620 (±1418) | 3 (±2) |
| 0.5 | 2,739 (±1359) | 30 (±19) |
| 1 | 2,629 (±1,129) | 15 (±2) |
| 2.5 | 11,665 (±2,989) | 94 (±66) |
| 112 | 82,424 (±49,208) | 103 (±50) |

*mean ± standard error of mean (n = 10 fish per group)

Example 5

Transfection of Fish Cells by Injection of Plasmid DNA Formulated With a Cationic Lipid Zebra fish were injected intraperitoneally (IP) (i.e., in the abdomen) with 0.1 μg of pCMV-luc alone or associated with 0.5 μg of a cationic lipid, G304 (obtained from Gibco BRL, New York, USA) in 10 μl.

Luciferase activity in muscle, gills, and viscera (liver, spleen, intestine, stomach, swim bladder, pyloric caecae, and ovary or testis) was measured 2.5 days after DNA injection. The fish tissues were prepared as described previously (Example 2).

Table 5 (below) shows that protein is expressed from DNA that is injected intraperitoneally into fish. Injection of plasmid DNA formulated with cationic lipid resulted in higher foreign protein expression in the viscera than injection of DNA alone. Muscle tissue, on the other hand, expressed greater levels of luciferase enzyme when the plasmid pCMV-luc DNA was injected without the cationic lipid. Therefore, a cationic lipid may increase transfection efficiency depending the target tissue.

TABLE 5

| Zebra Fish | Luciferase Activity (RLU/sec/mg of protein)* | |
|---|---|---|
| Tissue | DNA alone | DNA + lipid |
| Muscle | 151 (±127) | 32 (±10) |
| Gills | 15 (±15) | 8 (±8) |
| Viscera | 3 (±2) | 85 (±40) |

*mean ± standard error of mean (n = 10 fish per group)

Example 6

Comparison of Foreign Gene Expression after Injection of DNA in Fish and in Mice Fish and mice were injected intramuscularly with a range of 0.1 μg to 50.0 μg of pCMV-luc plasmid DNA in 50 μl. Total luciferase activity for the whole muscle of mouse or fish was assayed 2.5 days after injection. The fish and mouse tissues were prepared as described previously (Example 2).

For each dose of DNA, injected trout demonstrated higher levels of luciferase activity than injected mice (Table 6 below). In general, for a given dose of DNA, luciferase activity was approximately 100 times higher in fish than in mouse. Therefore, the knowledge that mice can be immunized against numerous diseases using doses of DNA within the range tested here, and the finding that fish muscle is more easily transfected and/or that fish muscle expresses transgenes more efficiently, indicate that fish should be good candidates for DNA-based immunization.

TABLE 6

| Dose of DNA (μg) | Luciferase Activity (RLU/sec total)* | |
|---|---|---|
| | mouse | trout |
| 0.01 | N/A | 65,898 (±30,774) |
| 0.1 | 1,649 (±542) | 327,724 (±177,583) |
| 1.0 | 5,466 (±1536) | 1,100,347 (±669,634) |
| 10 | 43,082 (±5,419) | 3,225,068 (±1,869,474) |
| 50 | 70,713 (±15,921) | 4,520,741 (±1,609,457) |

*mean ± standard error of mean (n = 5 for trout except for the 50 μg dose group for which n = 12; n = 10 for mouse groups)

Example 7

Expression of Plasmid DNA after Immersion of Fish in DNA-containing Solutions

Cationic lipid, G304, was obtained from Gibco BRL, New York. USA. Cationic polymer liposomes designated Q203, Q205, Q206, Q208, Q250, and QX were obtained from Qiagen GmbH, Hilden, Germany. Cationic polymer liposomes are composed of a mixture of cationic polymers and neutral lipids. Such transfection reagents were prepared as described in U.S. Provisional Patent Application entitled, "A Novel Class of Cationic Reagents for High Efficient and Cell-Type-Specific Introduction of Nucleic Acids into Eukaryotic Cells", incorporated by reference herein.

For example, a cationic polymer (either Q203, Q205, Q206, Q208, Q250 or QX, described below in Table 7) and a neutral lipid, dioleoyloxiphosphatidylethanolamine (DOPE) were mixed together for a final concentration of 2 mM in chloroform, which was then evaporated off in a rotary evaporator at 60° C. The mixture was dried for 10 minutes under a reduced pressure of 10 to 15 mbar. Under sterile conditions, endotoxin free deionized water was added to the mixture, which was then heated while stirring at 60° C.

Next, Q203, Q205, Q250, and QX were sonicated once for 300 seconds at 60° C. In the case of Q250, trans β carotene was added to a final concentration of 0.37 mM before sonication. Q206 and Q208 were not sonicated but were stirred at 60° C. until the solutions became transparent or slightly opalescent. The total concentration of DOPE+ cationic polymer for all liposomes was 2 mM. The concentration of DOPE in each liposome can be calculated by multiplying the X(DOPE) value in Table 7 by 2 mM so that, for example, Q203-containing liposomes are 1.7 mM DOPE and 0.3 mM Q203. Table 7 (below) summarizes the cationic polymer liposomes used in the methods of this invention.

TABLE 7

| Cationic Polymer Liposome Reagent | Cationic Polymers | X(DOPE) | Method of Preparation |
|---|---|---|---|
| Q203 | butandiyl-1,4-bis(octadecyl dimethylammonium bromide) | 0.85 | with sonication. |
| Q205 | butandiyl-1,4-bis(octadecyl dimethylammonium bromide) | 0.82 | with sonication. |
| Q206 | butandiyl-1,4-bis(octadecyl dimethylammonium bromide) | 0.78 | without sonication. |
| Q208 | butandiyl-1,4-bis(octadecyl dimethylammonium bromide) | 0.75 | without sonication. |
| Q250 | didodecyldimethyl ammonium bromide | 0.571 | with sonication. Add trans β carotene to final concentration of 0.37 mM. |
| QX | didodecyldimethyl ammonium bromide | 0.375 | with sonication. |

DNA:liposome complexes were prepared by independently diluting DNA and liposome solutions in 0.15M NaCl, then mixing the two solutions and vortexing, and then incubating the mixture at room temperature for 30–45 minutes. The solutions were diluted further with water and incubated for an additional 10–15 minutes at room temperature prior to use with fish.

Each fish was immersed in the solution of liposome formulated DNA (2.5 ml or 5 ml per fish) for 90 minutes and then returned to its normal holding tank. After 2.5 days, the fish were homogenized or gills and muscle were homogenized separately and assayed for luciferase activity.

Table 8 (below) shows luciferase activity above background in individual zebra fish after immersion. Thus, the results of Table 8 indicate that the majority of fish were successfully transfected and able to express foreign protein after immersion in DNA:liposome solutions. No fish expressed luciferase activity after immersion in pCMV-luc DNA without liposomes. Therefore, lipid-containing transfection reagents appear to significantly contribute to the transfection efficiency of DNA into fish with the immersion technique.

TABLE 8

| Transfection Reagent | Total Luciferase Activity (RLU/ second) |
|---|---|
| G304 | 330, 65, 0, 1643, 1581, 143, 5, 165, 0, 0, 257 |
| Q203 | 268, 82, 106, 264 |
| Q205 | 188, 268, 166, 136 |
| Q206 | 208, 286, 170, 108, 174 |
| Q208 | 668, 204, 1060, 0, 0, 180, 842, 242, 90, 36 |
| Q250 | 358, 398, 60, 10, 134, 1742, 54, 136, 84, 136 |
| QX | 166, 80, 302, 74, 432, 630, 28, 28, 260, 260 |

Example 8

Induction of an Immune Response against a Protein Derived from a Fish Pathogen in Fish and Mice by Injection of Antigen-Encoding Plasmid DNA Purified $pCMV_A$-VP3 DNA (encoding the VP3 protein of infectious pancreatic necrosis virus) was prepared as described previously for pCMV-luc DNA and injected intramuscularly in mice or trout. Each of three adult female BALB/C mice received 100 μg in tibialis anterior muscle while a single one-year old female trout received 200 μg in the tail muscle. Two weeks later, the humoral immune response against the expressed antigen was determined by ELISA assay of plasma taken from the mice and fish to detect anti-VP3 antibody.

The ELISA assay was performed using standard techniques. In particular, 96-well plates were coated with infectious pancreatic necrosis virus (IPNV) particles, blocked with a non-specific protein, and then washed. Ten-fold serial dilutions of trout or mice plasma and control plasma (obtained from non-injected mice and fish or from animals injected with control DNA not encoding VP3) were put in the appropriate wells (100 μl/well) were incubated for 2 hours. After washing, bound anti-VP3 antibodies in trout and mouse plasma were detected by addition of horse-radish peroxidase-labeled (HRP) mouse anti-trout or goat anti-mouse IgG monoclonal antibodies, respectively. Amounts of bound antibody were quantitated by reaction with O-phenylenediamine dihydrochloride, which is cleaved by HRP producing a color measurable by a spectrophotometer at $OD_{450}$.

ELISA titer values in Table 9 (below) indicate the dilution factor which gave an $OD_{450}$ value twice that of background. Table 9 shows that DNA-based immunization of fish or mice by intramuscular injection of plasmid DNA can induce an immune response against an antigenic protein of a fish pathogen such as the VP3 protein of IPNV.

TABLE 9

| Species | anti-VP3 ELISA titers |
| --- | --- |
| Mouse | 527.2 |
| Trout | 14.1 |

The collective results of the examples show the expression of foreign proteins in cells of fish after administration of pure plasmid DNA, either by intramuscular or intraperitoneal injection of pure or formulated plasmid DNA, or by injection of or immersion in DNA formulated with cationic liposomes. Furthermore, the collective results show that an immune response can be induced if the protein is antigenic, for example a protein of a fish pathogen. This should lead to protection against natural infection by virulent pathogen.

While we have hereinbefore presented a number of embodiments of this invention, it is apparent that our basic construction can be altered to provide other embodiments which utilize the methods of this invention. Therefore, it will be appreciated that the scope of this invention is to be defined by the claims appended hereto rather than the specific embodiments which have been presented hereinbefore by way of example.

What is claimed is:

1. A composition for inducing an immune response in finfish comprising:
   an expression vector having an expression control sequence capable of directing expression in finfish of at least one immunogenic polypeptide and a polypeptide-encoding DNA sequence encoding at least one immunogenic polypeptide from a fish pathogen.

2. The composition according to claim 1, wherein the vector additionally comprises an immunostimulatory unmethylated CpG motif.

3. The composition according to claim 1, wherein the injection of the vector comprising a fish pathogen induces a protective response in finfish.

4. The composition for inducing an response according to claim 1 or 3, wherein the vector is selected form the group consisting of pCMV-G, pCMV-N, pCMV-VP2, pCMV-VP3, pCMV-fstA, and.

5. The composition according to claim 1, wherein the polypeptide-encoding DNA sequence additionally encodes a different polypeptide from the same pathogen.

6. The composition according to claim 1, wherein the polypeptide-encoding DNA sequence additionally encodes a polypeptide from a different pathogen.

7. The composition according to claim 1, wherein the polypeptide-encoding DNA sequence additionally encodes a carrier polypeptide to form a fusion protein with the immunogenic polypeptide.

8. The composition according to claim 7, wherein the carrier polypeptide is a surface antigen of the human hepatitis B virus.

9. The composition according to claim 1, wherein the vector further comprises a second expression control sequence capable of directing expression of a polypeptide and a second polypeptide-encoding DNA sequence under transcriptional control of the second expression control sequence.

10. The composition according to claim 9, wherein the second polypeptide-encoding DNA sequence is a cytokine.

11. The composition for inducing an immune response according to claim 1 further comprising an immune modulator adjuvant.

12. The composition according to claim 11, wherein the adjuvant is an oligonucleotide having an immunostimulatory unmethylated CpG motif.

13. The composition according to claim 1 formulated with a transfection reagent.

14. The composition according to claim 13, wherein the transfection reagent is selected from the group consisting of liposomes, fluorocarbon emulsions, cochleates, tubules, gold particles, biodegradable microspheres, and cationic polymers.

15. The composition according to claim 14, wherein the transfection reagent is a liposome.

16. The composition according to claim 14, wherein the transfection agent is a cationic polymer.

17. The composition according to claim 1, wherein the immunogenic polypeptide is encoded in the genome of a rhabdovirus selected from the group of viral haemorrhagic septicaemina virus (VHSV), infectious haematopoietic necrosis virus (IHNV), and spring viraemia of carp virus (SVCV).

18. The composition according to claim 1, wherein the immunogenic polypeptide is encoded in the genome of a fish rhabdovirus selected from the group of viral haemorrhagic septicaemina virus (VHSV), infectious haematopoietic necrosis virus (IHNV), and spring viraemia of carp virus (SVCV).

19. The composition according to claim 1, wherein the immunogenic polypeptide is encoded in the genome of a birnavirus.

20. The composition according to claim 1, wherein the birnavirus is infectious pancreatic necrosis virus (IPNV).

21. The composition according to claim 1, wherein the immunogenic polypeptide is selected from the group consisting of VP1, VP2, VP3, and N structural proteins encoded in the genome of the infectious pancreatic necrosis virus (IPNV).

22. The composition according to claim 1, wherein the immunogenic polypeptide is encoded by the genome of a marine herpesvirus.

23. The composition according to claim 22, wherein the immunogenic polypeptide is encoded by the genome of the channel catfish virus (CCV).

24. The composition according to claim 23, wherein the immunogenic polypeptide is selected from the group consisting of an envelope protein, a membrane-associated protein) tegumin, a capsid protein, and a glycoprotein of the channel catfish virus (CCV).

25. The composition according to claim 1, wherein the immunogenic polypeptide is encoded by the genome of a marine nodavirus.

26. The composition of claim 25, wherein the nodavirus is selected from the group consisting of nervous necrosis virus and striped jack nervous necrosis virus.

27. The composition according to claim 1, wherein the immunogenic polypeptide is encoded by the genome of a iridovirus.

28. The composition according to claim 27, wherein the iridovirus is selected from the group consisting of fish lymphocystis disease virus (FLDV) and other marine iridoviruses.

29. The composition according to claim 1, wherein the immunogenic polypeptide is encoded by the genome of infectious salmon anaemia virus (ISAV).

30. The composition according to claim 1, wherein the immunogenic polypeptide is encoded by the genome of a bacterial pathogen selected from the group consisting of *Aeromonis salmonicida, Renibacterium salmoninarum, Vibrosis anguillarum* and *Vibrosis ordalii*, Yersiniosis, Pasteurellosis, *Edwardsiellosis ictaluri, Edwardsiellosis tarda, Cytophaga columnari*, and Rickettsia.

31. The composition according to claim 1, wherein the immunogenic polypeptide is selected from the group consisting of an iron-regulated outer membrane protein, (IROMP), an outer membrane protein (OMP), and an A-protein of *Aeromonis salmonicida*.

32. The composition according to claim 1, wherein the immunogenic polypeptide is selected from the group consisting of the p57 protein, major surface associated antigen (msa), a surface expressed cytotoxin (mpr), and a surface expressed hemolysin (ish) of *Renibacterium salmoninarum*.

33. The composition according to claim 1, wherein the immunogenic polypeptide is a flagellar antigen of Yersinosis.

34. The composition according to claim 1, wherein the immunogenic polypeptide is selected from the group consisting of an extracellular protein (ECP), an iron-regulated outer membrane protein (IROMP), and a structural protein of Pasteurellosis.

35. The composition according to claim 1, wherein the immunogenic polypeptide is selected from the group consisting of an outer membrane protein (OMP) and a flagellar protein of a member of the genus Vibrosis, wherein said member is selected from the group consisting of *Vibrosis anguillarum* and *Vibrosis ordalii*.

36. The composition according to claim 1, wherein the immunogenic polypeptide is selected from the group consisting of a flagellar protein, an outer membrane protein (OMP) protein, aroA, and purA of a member of the genus Edwardsiellosis, wherein said member is selected from the group consisting of *Edwardsiellosis ictaluri* and *E. tarda*.

37. The composition according to claim 1, wherein the immunogenic polypeptide is a structural or regulatory protein of *Cytophaga columnari*.

38. The composition according to claim 1, wherein the immunogenic polypeptide is a structural or regulatory protein of Rickettsia.

39. The composition according to claim 1, wherein the immunogenic polypeptide is encoded by the genome of a marine parasite.

40. The composition according to claim 39, wherein the marine parasite is a member of the genus Ichthyophthirius.

41. The composition according to claim 39, wherein the immunogenic polypeptide is surface antigen of the parasite Ichthyophthirius.

42. A method of inducing immune response in fin-fish against infection from fish pathogens, comprising administering to the fin-fish a composition for inducing an immune response comprising an expression vector having an expression control sequence capable of directing expression of an immunogenic polypeptide, and a polypeptide-encoding DNA sequence encoding an immunogenic polypeptide.

43. The method according to claim 42, wherein the vector additionally comprises a nucleic acid sequence comprising at least one unmethylated CpG motif, wherein the nucleic acid sequence is immunostimulatory.

44. The method according to claim 42, wherein the polypeptide-encoding DNA sequence additionally encodes a different polypeptide from the same pathogen.

45. The method according to claim 42, wherein the polypeptide-encoding DNA sequence additionally encodes a polypeptide from a different pathogen.

46. The method according to claim 42, wherein the polypeptide-encoding DNA sequence additionally encodes a carrier polypeptide to form a fusion protein with the immunogenic polypeptide.

47. The method according to claim 42, wherein the vector further comprises a second expression control sequence capable of directing expression of a polypeptide and a second polypeptide-encoding DNA sequence under transcriptional control of the second expression control sequence.

48. The method according to claim 42, wherein the composition is formulated with a transfection reagent selected from the group consisting of liposomes, fluorocarbon emulsions, cochleates, tubules, gold particles, biodegradable microspheres, and cationic polymers.

49. The method according to claim 42, further comprising administering to the fin-fish an additional DNA expression vector comprising an expression control sequence capable of directing expression of an immunogenic polypeptide and a polypeptide-encoding DNA sequence capable of inducing an immune response.

50. The method according to claim 42, further comprising administering to the fin-fish an adjuvant before or after administration of the composition.

51. The method according to claim 42, further comprising administering to the fin-fish a recombinant or purified protein, wherein said protein is administered before, during or after administration of the composition.

52. The method according to claim 42, wherein the composition is administered by intramuscular injection or intraperitoneal injection.

53. The method according to claim 42, wherein the composition is administered by immersion.

54. The method according to claim 53, wherein the DNA is formulated with a transfection reagent selected from the group consisting of cationic liposomes and cationic polymers.

55. The method according to claim 42, wherein the fin-fish is selected from the group consisting of salmon, salmonid, carp, catfish, trout (including rainbow trout), yellowtail, seabream, and seabass.

56. The method according to claim 42, wherein the pathogen is a viral fish pathogen.

57. The method according to claim 42, wherein said immunogenic peptide is encoded in the genome of a viral fish pathogen.

21

58. The method according to claim 42, wherein the immunogenic polypeptide is encoded in the genome of a rhabdovirus selected from the group of viral haemorrhagic septicaemina virus (VHSV), infectious haematopoietic necrosis virus (IHNV), and spring viraemia of carp virus (SVCV).

59. The method according to claim 42, wherein the immunogenic polypeptide is encoded in the genome of a birnavirus.

60. The method according to claim 59, wherein the birnavirus is an infectious pancreatic necrosis virus (IPNV).

61. The method according to claim 42, wherein the immunogenic polypeptide is selected from the group consisting of VP1, VP2, VP3, and N structural proteins encoded in the genome of the infectious pancreatic necrosis virus (IPNV).

62. The method according to claim 42, wherein the immunogenic polypeptide is encoded by the genome of a marine herpesvirus.

63. The method according to claim 62, wherein the immunogenic polypeptide is encoded by the genome of the channel catfish virus (CCV) 1.

64. The method according to claim 63, wherein the immunogenic polypeptide is an envelope protein of the channel catfish virus (CCV).

65. The method according to claim 42, wherein the immunogenic polypeptide is encoded by the genome of a marine nodavirus.

66. The method according to claim 65, wherein the nodavirus is selected from the group consisting of nervous necrosis virus and striped jack nervous necrosis virus.

67. The method according to claim 42, wherein the immunogenic polypeptide is encoded by the genome of a iridovirus.

68. The method according to claim 67, wherein the irridovirus is selected from the group consisting of fish lymphocystis disease virus (FLDV) and other marine iridoviruses.

69. The method according to claim 42, wherein the immunogenic polypeptide is encoded by the genome of infectious salmon anaemia virus (ISAV).

70. The method according to claim 42, wherein the immunogenic polypeptide is encoded by the genome of a bacterial pathogen selected from the group consisting of *Aeromonis salmonicida, Renibacterium salmoninarum, Vibrosis anguillarum* and *Vibrosis ordalii,* Yersiniosis, Pasteurellosis, *Edwardsiellosis ictuluri, Edwardsiellosis tarda, Cytophaga columnari,* and Rickettsia.

71. The method according to claim 42, wherein the immunogenic polypeptide is selected from the group consisting of an iron-regulated outer membrane protein, (IROMP), an outer membrane protein (OMP), and an A-protein of *Aeromonis salmonicida.*

22

72. The method according to claim 42, wherein the immunogenic polypeptide is selected from the group consisting of the p57 protein, major surface associated antigen (msa), a surface expressed cytotoxin (mpr), and a surface expressed hemolysin (ish) of *Renibacterium salmoninarum.*

73. The method according to claim 42, wherein the immunogenic polypeptide is a flagellar antigen of Yersinosis.

74. The method according to claim 42, wherein the immunogenic polypeptide is selected from the group consisting of an extracellular protein (ECP), an iron-regulated outer membrane protein (IROMP), and a structural protein of Pasteurellosis.

75. The method according to claim 42, wherein the immumogenic polypeptide is selected from the group consisting of an outer membrane protein (OMP) and a flagellar protein of a member of the genus Vibrosis, wherein said member is selected from the group consisting of *Vibrosis anguillarum* and *V. ordalii.*

76. The method according to claim 42, wherein the immunogenic polypeptide is selected from the group consisting of a flagellar protein, an outer membrane protein (OMP) protein, aroA, and purA of a member of the genus Edwardsiellosis, wherein said member is selected from the group consisting of *Edwardsiellosis ictaluri* and *E. tarda.*

77. The method according to claim 42, wherein the immunogenic polypeptide is a structural or regulatory protein of *Cytophaga columnari.*

78. The method according to claim 42, wherein the immunogenic polypeptide is a structural or regulatory protein of Rickettsia.

79. The method according to claim 42, wherein the immunogenic polypeptide is encoded by the genome of a marine parasite.

80. The method according to claim 79, wherein the marine parasite is a member of the genus Ichthyophthirius.

81. The method according to claim 42, wherein the immunogenic polypeptide is a surface antigen of the parasite *Ichthyophthirius multifiliis.*

82. A method for expressing a polypeptide in fin-fish comprising administering to a fin-fish a DNA expression vector comprising an expression control sequence capable of directing expression of a polypeptide and a polypeptide-encoding DNA sequence encoding at least one polypeptide from a fish pathogen.

83. The method according to claim 82, wherein said DNA expression vector is administered by a technique selected from the group consisting of intramuscular injection, intraperitoneal injection, or immersion.

* * * * *